United States Patent [19]

Vahlne et al.

[11] Patent Number: 4,812,556

[45] Date of Patent: Mar. 14, 1989

[54] SYNTHETIC PEPTIDE ANTIGEN FOR THE DETECTION OF HIV-2 INFECTION

[75] Inventors: Anders Vahlne, Hovas; Bo Svennerholm, Gothenburg; Lars Rymo, Hovas; Stig Jeansson; Peter Horal, both of Gothenburg, all of Sweden

[73] Assignee: Virovahl, Switzerland

[21] Appl. No.: 51,727

[22] Filed: May 18, 1987

[51] Int. Cl.[4] ................................................ C07K 7/10
[52] U.S. Cl. .................................................... 530/324
[58] Field of Search ......................................... 530/324

[56] References Cited

FOREIGN PATENT DOCUMENTS 87 04459  7/1987  France .

OTHER PUBLICATIONS

Chem. Abstr. vol, 108 (1988) 20148.
Chem. Abstr. vol. 107 (1987) 234335.
Kanki et al., Science, vol. 236, pp. 827–832, 1987.
Benn et al., Science, vol. 230, pp. 949–951, 1985.
Kanki et al., Science, vol. 228, pp. 1199–1201, 1985.
Kanki et al., Science, vol. 230, pp. 951–954, 1985.
Kanki et al., Science, vol. 232, pp. 238–243, 1986.
Daniel et al., Science, vol. 228, pp. 1201–1204, 1985.
Clavel et al., Science, vol. 233, pp. 343–346, 1986.
Clavel et al., N. Engl. J. Med., vol. 316, pp. 1180–1185, 1987.
Guyader et al., Nature, vol. 326, pp. 662–669, 1987.
Cabradilla et al., Biotechnology, vol. 4, pp. 128–133, 1986.
Chang et al., Biotechnology, vol. 3, pp. 905–909, 1985.
Putney et al., Science, vol. 234, pp. 1392–1395, 1986.
Kieny et al., Biotechnology, vol. 4, pp. 790–795, 1986.
Lerner, Adv. Immunol. vol. 36, pp. 1–45, 1984.
Erickson et al., Chapter 3, *The Proteins*, 3rd edit., 1976.
*The Users Manual for Peptide Synthesizer Model 430A*.
Lerner et al., in *The Biology of Immunological Disease: A Hospital Practice Book*, pp. 331–338, 1983.
Merrifield and Barany, Chapter 1, *The Peptides: Analysis Synthesis*, Biology, vol. 1, 1980.

*Primary Examiner*—Delbert R. Phillips
*Attorney, Agent, or Firm*—Brumbaugh, Graves, Donohue & Raymond

[57] ABSTRACT

A synthetic peptide antigen corresponding to a region of the glycoprotein gp41 encoded by the env gene of HIV-2 is provided. The peptide which is immunologically reactive with HIV-2 specific antibodies is useful in assays for detection of HIV-2 infection or exposure and in compositions to elicit the production of antibodies against HIV-2 in animals including man.

2 Claims, No Drawings

SYNTHETIC PEPTIDE ANTIGEN FOR THE DETECTION OF HIV-2 INFECTION

BACKGROUND OF THE INVENTION

The present invention relates to a synthetic peptide antigen the sequence of which corresponds to a region of an immunologically important protein of HIV-2. This peptide is useful as a diagnostic reagent for detecting the presence of antibodies to HIV-2. The peptide may also be useful as an immunogen in compositions to elicit the production of antibodies against HIV-2 in animals including man.

The acquired immunodeficiency syndrome (AIDS) is a major worldwide health problem. The etiologic agent of AIDS has been identified as HIV (for human immunodeficiency virus) which is the name given to a group of highly related viruses, formerly called HTLV-III, LAV and ARC (now collectively HIV-1).

HIV isolates from individuals with AIDS and ARC (AIDS-related complex) from North America, Western Europe and Central Africa generally have the same biological properties and antigenically cross-reacting proteins. Genetic studies, however, have characterized differences in nucleotide sequence of the genomes of North American and African HIV isolates (Benn et al., Science (1985) 230:949–951). In addition, small differences in nucleotide sequences in different HIV isolates from the USA have also been documented.

Several other viruses that are genetically and structurally related to HIV have been recently isolated. These viruses which genetically and immunologically resemble HIV have been isolated from captive rhesus macaques (*Macaca mulatta*) ill with an AIDS-like disease and healthy wild-caught African green monkeys (*Cercocithecus* sp.) (Kanki et al., Science (1985) 230:951–954). The viruses which were previously designated STLV-III$_{AGM}$ (Africa green monkey isolate) and STLV-III$_{MAC}$ (macaque isolate) are now known as SIV (for simian immunodeficiency virus).

A new human virus, designated HTLV-IV, has been isolated from apparently healthy individuals in West Africa (Kanki et al., Science (1986) 232:238–243. This virus, which produces retroviral type particles in infected cells, has growth characteristics and major viral proteins that are similar to those of HTLV-III/LAV and STLV-III. Serologic data indicated that HTLV-IV is more related to STLV-III$_{AGM}$ than to the prototype HTLV-III/LAV isolates from patients in Europe and the United States.

Recently, cases of AIDS were identified in West African patients. Although the individuals had classic symptoms of AIDS, no detectable titers of antibodies to known HIV antigens could be detected in patient sera. However, a retrovirus originally termed LAV-2 which is structurally and biolgically related to HIV was isolated from the West African patients (Clavel et al., Science (1986) 233: 343–346. The West African virus, which has now been isolated from a number of individuals with AIDS, ARC and no symptoms, is now known as HIV-2 to distinguish it from HIV (now HIV-1) isolates previously identified as the etiologic agent of AIDS in Europe, North America and Central Africa (Clavel et al., *N. Eng. of Med.* (1987) 316:1180–1185; Guyader et al. *Nature* (1987) 326:662–669).

Like HTLV-IV, HIV-2 is more related to SIV than to HIV-1. However, HIV-2 and HTLV-IV are not the same virus since HIV-2 kills human helper T cells infected in vitro whereas HTLV-IV does not.

The complete nucleotide sequence of HIV-2 which has recently been reported (Guyader et al., supra) indicates a genetic sequence homology with HIV-1 of only 42%. Significant differences occur in most viral protein but are most pronounced in the glycoproteins encoded by the HIV-1 and HIV-2 env genes. In fact, the HIV-2 envelope glycoproteins appear to be more closely related to those of SIV than to HIV-1.

The issue of serologic non cross-reactivity between HIV-1 and HIV-2 is of major importance in developing diagnostic tests for detection of and vaccines against HIV-2 infection. Studies have shown that the patients with HIV-2 infections were not identified by serologic tests which detect HIV-1. Any cross reactions which have been seen for the two viruses generally are mediated by antibodies which react with common epitopes on the major core proteins, p25 and p26, encoded by the gag gene of the two viruses. Antibodies to the viral envelope glycoproteins gp120 and gp41 and their precursor gp160 of HIV-1 do not cross-react with the envelope glycoproteins of HIV-2 (Clavel et al., Science (1986) 233:343–346; Clavel et al., *N. Engl. J. Med.* (1987) 316:1180–1185). Currently available tests for detection of HIV-1, which are mainly based on detection of antibodies to the HIV-1 glycoproteins, e.g., gp160/gp120/gp41, and portions thereof, cannot be used to detect antibodies to HIV-2 in samples for diagnostic and screening purposes. Thus specific HIV-2 antigens should be included with HIV-1 antigens in reagents for effective diagnostic and therapeutic use.

Methods being developed for detecting HIV-2 infection, in general, will measure exposure to the virus by detecting and quantifying antibodies to HIV-2 antigens in blood, sera, and blood-derived products. Such assays can be used to aid diagnosis of AIDS and ARC (AIDS-Related Complex) and to screen blood and blood products for previous exposure to HIV-2.

The current attempts to diagnose HIV-2 infections and screen blood for exposure to HIV-2 include enzyme-linked immunosorbent assay (ELISA) techniques to detect the presence of antibodies to immunogenic components of HIV-2 in a test sample. Other methods may utilize Western blotting techniques to detect HIV-2 specific antibodies in test samples. In general, almost any known immunoassay, such as radioimmunoassays, can be adapted, by use of specific reagents, for the detection of HIV-2 and antibodies thereto.

The source of antigens for these assays may include inter alia HIV-2 proteins obtained from HIV-2 infected T cell lines and antigens produced by recombinant DNA techniques. The use of antigens obtained from these sources, however, has significant drawbacks.

The production of HIV-2 per se in continuous cell lines must be performed in high risk (P3 containment) laboratories due to the danger to investigators who may become adversely exposed to the virus. In addition, since there have been false negative and false positive results reported with ELISA tests using whole virus HIV-1 antigens obtained from cell lines; it is likely that similarly unreliable results will be obtained with cell-derived HIV-2 antigens. Western blot analyses, for HIV-2 detection using electroblotted whole virus antigens, may provide greater specificity but are more laborious and time-consuming then ELISA tests. Furthermore, since HIV-2 producing cells are of human origin, viral antigen preparation obtained from these cell lines, unless exhaustively purified, may be contaminated with normal cellular antigens, such as HLA antigens, which could produce false positive reactions in an ELISA test.

Exhaustive purification of viral antigens from cell lines can also conceivably destroy immunogenicity of immunologically important proteins or otherwise inactivate antigens, thereby producing reagents that result in false negative reactions. In addition, false negative reactions using live-virus-derived antigens may occur because of steric hinderance whereby antibodies cannot react with their specific antigens because the reaction is blocked by the presence of other antigens and antibodies in the reaction mixture.

ELISA tests to detect HIV-2 infection may also employ immunologically important viral proteins produced by cloning portions of the HIV-2 genome in bacteria. The complete nucleotide sequence of HIV-2 has now been reported (Guyander et al., *Nature* (1987) 326: 662-669) with the genes coding for various HIV-2 proteins identified by comparison to homologous HIV-1 genes. The viral envelope glycoproteins and core proteins respectively encoded by the env and gag genes of HIV-2, are apparently the antigens recognized by antibodies in the sera of patients with HIV-2 infection.

Immunologically important HIV-2 antigens such as gp160 and its cleavage products gp120 and gp41, which are present in the viral envelope, may be prepared by cloning portions of the HIV-2 genome in various expression systems such as bacteria, yeast or vaccinia. Such recombinant antigens may be used in diagnosis and as potential vaccine compositions as has been done for HIV-1 proteins (See, e.g., Cabradilla et al., *Biotechnology* (1986)4: 128-133; Chang et al., *Biotechnology* (1985) 3: 905-909; Putney et al., *Science* (1986) 234: 1392-1395; Kieny et al. *Biotechnology* (1986) 4: 790-795). HIV-2 antigens produced by recombinant DNA methods, however, will still have to be exhaustively purified to avoid false positive reactions in the ELISA due to any antibody reactivity to antigens of the expression system which may contaminate the HIV-2 antigen preparation. Also, denaturation of HIV-2 antigens during purification may destroy important antigen activity.

While HIV-2 antigens produced by recombinant techniques may be an improvement over antigens obtained from virus-infected cell cultures, the recombinant proteins still may not provide reagents that give as accurate a diagnosis as possible. Because of the nature of the disease and the need for accurate results, other reagents must be developed to approach 100% accuracy in diagnosis of HIV-2.

Protein antigens contain a number of epitopes or antigenic determinants which are the regions of the proteins which comprise the binding sites for specific antibodies. In general, protein antigens contain between 5 to 10 epitopes, each of which contains a sequence of 6 to 8 amino acids. Epitopes can be either continuous, in which the 6 to 8 amino acids are present in linear sequence, or discontinuous, in which the amino acids that form the epitope are brought together by the three dimensional folding of the protein. Even though an epitope constitutes only a relatively few amino acids, its reactivity with an antibody is influenced by the amino acids in the protein which surround the epitope.

Studies aimed at mapping antigenic sites or epitopes of proteins have been aided by the use of synthetic peptides corresponding to various regions of the proteins of interest (See e.g., Lerner et al., in *The Biology of Immunological Disease: A Hospital Practice Book*, (1983) Dixon and Fisher, eds., pp. 331-338; Lerner, *Adv. Immunol.* (1984) 36: 1). In addition to their usefulness in epitope mapping studies, synthetic peptides, if encompassing major antigenic determinants of a protein, have potential as immunogenic compositions, including vaccines, and diagnostic reagents. Synthetic peptide antigens have several advantages in regard to specific antibody production and reactivity. The exact sequence of the synthesized peptide can be selected from the amino acid sequence as actually determined by amino acid sequencing of a protein or predicted from the DNA sequence coding for the protein. The use of specific synthetic peptides eliminate the need for using the full-length protein in the production of or assay for specific antibodies. Furthermore, the solid phase peptide synthetic techniques of Merrifield and coworkers allow for essentially unlimited quantities of the synthesized peptide of interest to be chemically produced. (See, e g., Erickson and Merrifield in *The Proteins*, 3rd Edit. (1976), Vol. 2, Academic Press, New York, Chapter 3). The availability of automated peptide synthesizers has further advanced such techniques.

Synthetic peptide antigens corresponding to regions of immunologically important proteins of HIV-2 would find immediate use in diagnostic methods and as potential vaccines for HIV-2.

SUMMARY OF THE INVENTION

In accordance with the present invention, a novel synthetic peptide corresponding to an antigenic HIV-2 protein is provided which is useful in selective diagnostic methods for detecting HIV-2 infections.

A novel synthetic peptide antigen corresponding to a portion of glycoprotein gp41 encoded by the HIV-2 env gene has now been found. The peptide is useful for diagnosing AIDS caused by HIV-2 infection in suspected individuals and in methods for screening for exposure to HIV-2 in blood and blood-derived products with a high degree of reliability and specificity.

The peptide can b used in methods of detecting antibodies to HIV-2 in samples. The methods involve contacting the sample with the peptide antigens under conditions which allow an immunological complex to form between the peptide and any HIV-2 specific antibodies which may be present in the sample. Measuring of complex formation if any by suitable detection means indicates the presence or absence of antibodies to HIV-2 in the sample.

The novel peptide may also be used as an immunogen in vaccine compositions for immunization against HIV-2 infection or for the production in animals of HIV-2 specific antibodies against HIV-2 antigens.

DESCRIPTION OF THE INVENTION

The present invention provides a peptide corresponding to a region of the transmembrane envelope glycoprotein gp41 of HIV-2 which has been synthesized and tested for immunoreactivity to HIV-2 positive serum samples. The novel peptide is useful in tests to diagnose HIV-2 infection or prior exposure to the virus and as an immunogen in compositions to elicit the production in animals including man of antibodies against HIV-2. The peptide encompassed by the invention comprises an amino acid sequence containing therein at least one continuous (linear) epitope reactive with HIV-2 specific antibodies.

The invention thus encompasses an immunologically reactive peptide and functionally equivalent variants thereof which do not significantly affect the antigenic properties of the peptide corresponding to a region of gp41 encoded by the env gene of HIV-2. The peptide was synthesized by known solid phase peptide synthesis techniques (see e.g., Merrifield and Barany, *The Peptides: Analysis, Synthesis, Biology* (1980), Vol. 1, Gross and Meinenhofer, eds., Academic Press, New York, Chap. 1). The synthesis also allows for one or two amino acids not corresponding to the original protein sequence to be added to the amino or carboxyl terminus of the peptide. Such extra amino acids are useful for coupling the peptide to another peptide, to a large carrier protein or to a support. Amino acids that are useful for these purposes include tyrosine, lysine, glutamic acid, aspartic acid, cysteine and derivatives thereof. Additional protein modification techniques may be used, e.g., $NH_2$-acetylation or COOH-terminal amidation, to provide additional means for coupling the peptide to another protein or peptide molecule or to a support.

The novel peptide sequence is set forth below:

H2-41A5

X-Asp-Gln-Ala-Arg-Leu-Asn-Ser-Trp-Gly-Cys-Ala-Phe-Arg-Gln-Val-Cys-His-Thr-Thr-Val-Pro-Trp-Val-Asn-Y-Z, wherein X is either a H of the amino terminal $NH_2$ group of the peptide or an additional amino acid bonded to the amino terminal $NH_2$ group of the peptide, the additional amino acid being selected to facilitate coupling of the peptide to a carrier protein; Y is absent or Cys; and Z is OH or $NH_2$.

Peptide H2-41A5 is encoded by the nucleotide sequence of the HIV-2 genome encompassing base pairs (bp) 7908 through 7978 (numbering of Guyader et al., *Nature* (1987) 326:662–669) which is in a region of the env gene coding for gp41. Peptide H2-41A5 in which X is H, Y is Cys and Z is OH is particularly preferred.

The peptide can be used in methods for detection of antibodies to HIV-2 or HIV-2 associated antigens. Preferably the methods which use the peptide to detect the presence of HIV-2 specific antibodies in the sample involve contacting the sample with the peptide under conditions to allow the formation of an immunological complex between the peptide antigen and any antibodies to HIV-2 that may be present in the sample. The formation of an immunological complex, if any, indicating the presence of antibodies to HIV-2 in the sample, is then detected and measured by suitable means.

Such methods include, inter alia, homogeneous and heterogeneous binding immunoassays, such as radioimmunoassays (RIA), ELISA and Western blot analyses. Further, the assay protocols using the novel peptide allow for competitive and non-competitive binding studies to be performed.

The peptide may be labeled (signal-generating) or unlabeled depending on the type of assay used. Labels which may be coupled to the peptides are those known in the art and include inter alia enzymes, radionuclides, fluorogenic and chromogenic substrates, cofactors, biotin/avidin, colloidal gold, and magnetic particles. Modification of the novel peptide, allows for coupling by known means to carrier proteins or peptides or to known supports, for example, polystyrene or polyvinyl microtiter plates, glass tubes or glass beads and chromatographic supports, such as paper, cellulose and cellulose derivates, and silica.

Preferred known assay techniques, especially for large-scale clinical screening of patient sera and blood and blood-derived products are ELISA and Western blot techniques, ELISA tests being particularly preferred. The ELISA tests employing peptide H2-41A5 described above are based on those currently in use with human cell-derived or recombinant DNA-derived HIV-1 proteins or portions thereof as antigens. For use as reagents in these assays, peptide H2-41A5 is conveniently bonded to the inside surface of microtiter wells. The peptide may be directly bonded to the microtiter well. It has been found, however, that maximum binding of the peptide to the wells can be accomplished by pretreating the wells with polylysine prior to the addition of the peptide. Additionally, peptide H2-41A5 may be covalently attached by known means to a carrier protein, such as BSA, with the resulting conjugate being used to coat the wells. Generally the peptide was used in a concentration of from 10 to 100 μg/ml for coating.

Samples to be tested for antibodies to HIV-2 are then added to the peptide-coated wells where an immunological complex forms if antibodies to HIV-2 are present in the sample. A signal generating means may be added to aid detection of complex formation. A detectable signal is produced if HIV-2 specific antibodies are present in the sample.

The invention is further illustrated by the following specific examples which are not intended in any way to limit the scope of the invention.

EXAMPLE 1

An Applied Biosystems peptide-synthesizer Model 430 A, was utilized for the synthesis of peptide H2-42A5. The synthesis used a p-methylbenzylhydrylamine solid phase support resin (Peptides International, Louisville, Ky.). Peptide H2-41A5 was synthesized according to *The Users Manual for Peptide Synthesizer Model 430A*, Applied Biosystems, 1986. All amino acids for use in synthesis contained t-butylcarbonyl groups (t-Boc) protecting the α-$NH_2$ group and were obtained from Novabiochem AG, Switzerland. Amino acids with reactive side chain groups contained additional protective groups to prevent unwanted and undesirable side chain reactions. The individual protected amino acids used for synthesis of peptide H2-41A5 were selected from those set forth in Table 1. Boc-Glu(OBzl)-OH, Boc-Ile-OH ½ $H_2O$, Boc-Lys(2-Cl-Z)-OH (cryst.), Boc-Met-OH, and Boc-Tyr-(2-Br- Z)-OH were not utilized in the synthesis of peptide H2-41A5.

TABLE 1

| Amino Acids Used in Peptide Synthesis |
|---|
| Boc—Ala—OH |
| Boc—Arg (Tos)—OH |
| Boc—Asn—OH |
| Boc—Asp (OBzl)—OH |
| Boc—Cys (pMeOBzl)—Oh |
| Boc—Glu (OBzl)—OH |
| Boc—Gln—OH |
| Boc—Gly—OH |
| Boc—His(Tos)—OH |
| Boc—Ile—OH.½$H_2O$ |
| Boc—Leu—OH.$H_2O$ |
| Boc—Lys (2-Cl—Z)—OH (cryst.) |
| Boc—Met—OH |
| Boc—Phe—OH |
| Boc—Pro—OH |
| Boc—Ser(Bzl)—OH.DCHA |

TABLE 1-continued
Amino Acids Used in Peptide Synthesis

Boc—Thr (Bzl)—OH
Boc—Trp (Formyl)-OH
Boc—Tyr(2-Br—Z)—OH
Boc—Val—OH

Tos = Tosyl or p-Toluene sulfonic acid
oBzl = Benzyloxy
pMeoBzl = p-Methylbenzyloxy
2-Cl—Z = Carbobenzoxy chloride
2-Br—Z = Carbobenzoxybromide After completion of synthesis, the protecting groups were removed from the synthesized peptide and the peptide cleaved from the solid support resin by treatment at 0° C. with anhydrous hydrofluoric acid (HF) combining 10% anisole and 10% dimethylsulfide as scavenging agents. 2% thiocresol was added as an additional scavenger because H2-41A5 is a cysteine-containing peptide. After cleavage, the HF in the sample was purged under a stream of $N_2$, with removal of any residual HF accomplished by subjecting the sample to a vacuum at 0° C. The peptide was extracted from the resin by treatment with trifluoroacetic acid (TFA) which was then removed by evaporation at room temperature. Following TFA removal, the peptide was precipitated and washed with anhydrous ether.

Prior to use in specific assays, the peptide can be further purified, if desired, by reverse phase high performance liquid chromatography (HPLC). A particularly suited column for such purification is the reverse-phase Vydek® C-18 column using a water (TFA) - acetonitrile (TFA) gradient to elute the peptide.

EXAMPLE 2

Peptide H2-41A5 having the amino acid sequence Asp-Gln-Ala-Arg-Leu-Asn-Ser-Trp-Gly-Cys-Ala-Phc-Nrg-Gln-Val-Cys-His-Thr-Thr-Val-Pro-Trp-Val-Asn-Cys-OH was synthesized as described in Example 1 and used in an ELISA test to measure its immunologic reactivity.

Polylysine at a concentration of 1 mg/ml was added to the microtiter plates and allowed to incubate for 30 minutes. The polylysine was then discarded and peptide H2-41A5 was added to the wells of the plate in a concentration of 10 to 100 μg/ml for coating. After the peptide incubated in the well for a length of time sufficient to allow the peptide to be bonded to the well, the peptide solution was removed and a solution of glutaraldyhyde, which stabilizes the peptide attachment to the wells, was added for 15 minutes. The glutaraldehyde solution was then removed, the wells washed with buffer, and a mixture of glycine and bovine serum albumin (BSA) was added which served to block unbound sites in the wells and minimize non-specific binding of antibodies during the ELISA assay per se. After a final washing step, the plates were ready to use.

A convenient variation of known ELISA methods was used with the microtiter plates prepared as above. Serum samples from individuals which had been diluted 1:50 in PBS (phosphate buffered saline) containing 0.05% polyoxyethylenesorbitan monolaurate (Tween 20) and 1% BSA were added to each well and allowed to incubate for 90 minutes at 37° C. in a humidified atmosphere. The diluted serum samples were then removed from the plates and the wells washed three times with PBS containing 0.05% Tween 20. A conjugated anti-human Ig antibody was then added to the wells and allowed to incubate for 90 minutes. The conjugated antibody was produced in a goat or rabbit and was specific for human IgG, IgM, immunoglobulin light chains, or combinations thereof. Preferably, alkaline-phosphatase conjugated anti-human IgG (from Dakopatts) diluted 1:500 for use in PBS containing 0.05% Tween 20 and 1% BSA was used in the ELISA. After the conjugate had incubated a sufficient length of time to react with bound human antibodies, the plates were washed three times as above. In order to detect antibodies to HIV-2 in the human serum that react with the peptide H2-41A5 used as the antigen, (i.e. positive reactions), a chromogenic substrate alkaline phosphatase substrate (Sigma Cat. No. 104 tablets) dissolved in a Na carbonate/MgCl buffer and adjusted to a concentration of 1 μg/ml which was cleaved by the enzyme attached to the anti-human Ig to yield a colored product was added. After incubation for approximately 40 minutes at room temperature, positive reactions indicated the presence of antibodies in the sample reactive with the antigen. A yellow to orange to reddish-brown color in each well indicating a positive reaction, was read in a spectrophotometer at 405nm to quantify the reaction. Spectrophotometric readings were adjusted to correct for background reactions.

Peptide H2-41A5 was run in parallel ELISA tests against 6 serum samples positive for antibodies to HIV-2 (obtained from Dr. G. Biberfelt, SBL, Stockholm, Sweden), 10 serum samples positive for antibodies to HIV-1 and 6 HIV-1/HIV-2 negative sera. As shown in Table 2, 6/6 confirmed positive HIV-2 serum samples (100%) reacted with peptide H2-41A5. The table also shows that none of the HIV-1 positive serum samples and none of the negative sera reacted with H2-41A5.

It is evident from the foregoing results that the novel synthetic peptide, H2-41A5 described herein, which corresponds to a region of the HIV-2 glycoprotein gp41 encoded by the env gene, clearly provides a unique reagent for a sensitive and selective assay for the presence of antibodies to HIV-2.

TABLE 2
Immunoreactivity of Peptide H2-41A5 for HIV-2, Positive HIV-1 and Positive and Negative Serum Samples Determined by ELISA

| | $O.D._{405}$* |
|---|---|
| Confirmed HIV-2 Positive Serum, Sample # | |
| 449 | 2.584 |
| 2358 | 2.503 |
| N-3 | 1.872 |
| N-15 | 2.311 |
| N-20 | 2.139 |
| N-21 | 2.170 |
| Confirmed HIV-1 Positive Serum, Sample # | |
| 2 | 0.190 |
| 3 | 0.084 |
| 4 | 0.089 |
| 6 | 0.079 |
| 10 | 0.171 |
| 11 | 0.090 |
| 12 | 0.076 |
| 17 | 0.079 |
| 18 | 0.109 |
| 19 | 0.089 |
| Negative Serum, Sample # | |
| 39477 | 0.058 |
| 39478 | 0.080 |
| 39479 | 0.104 |
| 39481 | 0.070 |
| 39482 | 0.039 |

TABLE 2-continued

Immunoreactivity of Peptide H2-41A5 for HIV-2, Positive HIV-1 and Positive and Negative Serum Samples Determined by ELISA

| | O.D._{405}* |
|---|---|
| 39483 | 0.075 |

*Peptide H2-41A5 was coated at a concentration of 10 μg/ml.

We claim:

1. An antigenic peptide of the formula: Asp-Gln-Ala-Arg-Leu-Asn-Ser-Trp-Gly-Cys-Ala-Phe-Arg-Gln-Val-Cys-His-Thr-Thr-Val-Pro-Trp-Val-Asn-Y-Z, wherein X is either a H of the amino terminal NH$_2$ group of the peptide or an additional amino acid bonded to the amino terminal N$_2$ group of the peptide, the additional amino acid being selected to facilitate coupling of the peptide to a carrier protein; Y is absent or CYS; and Z is OH or NH$_2$.

2. An antigenic peptide of the formula Asp-Gln-Ala-Arg-Leu-Asn-Ser-Trp-Gly-Cys-Ala-Phe-Arg-Gln-Val-Cys-His-Thr-Thr-Val-Pro-Trp-Val-Asn-Cys-OH.

* * * * *

UNITED STATES PATENT AND TRADEMARK OFFICE
CERTIFICATE OF CORRECTION

PATENT NO. : 4,812,556

DATED : March 14, 1989

INVENTOR(S) : Vahlne et al.

It is certified that error appears in the above-identified patent and that said Letters Patent is hereby corrected as shown below:

```
Column 1, line 37, "Cerocithecus" should read --Cercopithec--;
Column 2, line 66, "then" should read --than--;
Column 4, line 42, "b" should read --be--;
Column 6, line 37, "42A5" should read --41A5--;
Column 8, line 45, the heading "O.D.405*" should be moved to
line 47, to coincide with the other heading.
```

Signed and Sealed this

Second Day of January, 1990

Attest:

JEFFREY M. SAMUELS

Attesting Officer     Acting Commissioner of Patents and Trademarks

UNITED STATES PATENT AND TRADEMARK OFFICE
CERTIFICATE OF CORRECTION

PATENT NO. : 4,812,556
DATED : March 14, 1989
INVENTOR(S) : Vahlne et al.

It is certified that error appears in the above-identified patent and that said Letters Patent is hereby corrected as shown below:

<u>Col. 1, line 44</u>, "232:238-243." should read --232:238-243).--;

<u>line 59</u>, "233:  343-346." should read --233:343-346).--;

<u>Col. 3, line 34</u>, "(1986)4:  128-133;" should read --(1986) 4:128-133;--;

<u>line 35</u>, "3:  905-909;" should read --3:905-909--;

<u>Col. 4, line 4</u>, "36:  1)." should read --36:1).--;

<u>Col. 10, line 1</u>, "Asp-Gln-Ala-" should read --X-Asp-Gln-Ala--;

<u>line 6</u>, "$N_2$" should read --$NH_2$--;

<u>line 9</u>, "CYS" should read --Cys--;

Signed and Sealed this

Twenty-fourth Day of April, 1990

Attest:

HARRY F. MANBECK, JR.

*Attesting Officer*     Commissioner of Patents and Trademarks